(12) United States Patent
Kleinfelter (10) Patent No.: US 7,069,226 B1
(45) Date of Patent: Jun. 27, 2006

(54) PRESCRIPTION DATA PROCESSING SYSTEM FOR DETERMINING NEW THERAPY STARTS

(75) Inventor: William M. Kleinfelter, Ivyland, PA (US)

(73) Assignee: Synetic, Incorporated, Elmwood Park, NJ (US)

( * ) Notice: Subject to any disclaimer, the term of this patent is extended or adjusted under 35 U.S.C. 154(b) by 608 days.

(21) Appl. No.: 09/348,774

(22) Filed: Jul. 7, 1999

(51) Int. Cl.
*G06F 17/60* (2006.01)

(52) U.S. Cl. .............................. 705/2; 705/3
(58) Field of Classification Search .................... 705/2, 705/3
See application file for complete search history.

(56) References Cited

U.S. PATENT DOCUMENTS

| | | | |
|---|---|---|---|
| 4,766,542 A | 8/1988 | Pilarczyk |
| 4,847,764 A | 7/1989 | Halvorson |
| 5,072,383 A | 12/1991 | Brimm et al. |
| 5,077,666 A | 12/1991 | Brimm et al. |
| 5,267,155 A | 11/1993 | Buchanan et al. |
| 5,277,188 A | 1/1994 | Selker |
| 5,291,399 A | 3/1994 | Chaco |
| 5,299,121 A | 3/1994 | Brill et al. |
| 5,301,319 A | 4/1994 | Thurman et al. |
| 5,324,718 A | 6/1994 | Loftsson |
| 5,325,478 A | 6/1994 | Shelton et al. |
| 5,327,341 A | 7/1994 | Whalen et al. |
| 5,337,919 A | 8/1994 | Spaulding et al. |
| 5,410,704 A | 4/1995 | Norden-Paul et al. |
| 5,459,536 A | 10/1995 | Shalon et al. |
| 5,465,082 A | 11/1995 | Chaco |
| 5,468,110 A | 11/1995 | McDonald et al. |
| 5,471,382 A | 11/1995 | Tallman et al. |
| 5,472,954 A | 12/1995 | Loftsson |
| 5,502,944 A | 4/1996 | Kraft et al. |
| 5,519,607 A | 5/1996 | Tawil |
| 5,542,420 A | 8/1996 | Goldman et al. |
| 5,546,472 A | 8/1996 | Levin |
| 5,558,638 A | 9/1996 | Evers et al. |
| 5,583,831 A | 12/1996 | Churchill et al. |
| 5,590,038 A | 12/1996 | Pitroda |
| 5,593,267 A | 1/1997 | McDonald et al. |
| 5,594,786 A | 1/1997 | Chaco et al. |
| 5,596,994 A | 1/1997 | Bro |

(Continued)

FOREIGN PATENT DOCUMENTS

WO    WO 9512812 A1 *  5/1995

OTHER PUBLICATIONS

Anonymous, Apr. 16, 2001, New Product Newswire, Drug Topics; Oradell, Medical Economics Inc., vol. 145, Issue 8, pp. 74-77.*

(Continued)

*Primary Examiner*—Joseph Thomas
*Assistant Examiner*—Robert W. Morgan
(74) *Attorney, Agent, or Firm*—Brown Raysman Millstein Felder & Steiner (57) ABSTRACT

Prescription data representing a prescription for a particular drug is arranged into records. Each record includes fields for identifying a patient and a subscriber, and for indicating the date for dispensing the drug and the drug dosage, among other things. Based on the information in the fields, a prescribed drug is identified as a new therapy or a continuation therapy. In addition, a therapy switch is ascertained on the basis of the drug identified as the new therapy for a patient.

49 Claims, 6 Drawing Sheets

U.S. PATENT DOCUMENTS

| | | |
|---|---|---|
| 5,597,995 A | 1/1997 | Williams et al. |
| 5,612,869 A | 3/1997 | Letzt et al. |
| 5,613,106 A | 3/1997 | Thurman et al. |
| 5,619,991 A | 4/1997 | Sloane |
| 5,623,242 A | 4/1997 | Dawson, Jr. et al. |
| 5,629,981 A | 5/1997 | Nerlikar |
| 5,633,368 A | 5/1997 | Hirsenkorn |
| 5,666,492 A * | 9/1997 | Rhodes et al. ............... 705/3 |
| 5,671,282 A | 9/1997 | Wolff et al. |
| 5,671,362 A | 9/1997 | Cowe et al. |
| 5,682,142 A | 10/1997 | Loosmore et al. |
| 5,689,229 A | 11/1997 | Chaco et al. |
| 5,689,247 A | 11/1997 | Welner |
| 5,692,125 A | 11/1997 | Schloss et al. |
| 5,694,806 A | 12/1997 | Martin et al. |
| 5,700,998 A | 12/1997 | Palti |
| 5,704,044 A | 12/1997 | Tarter et al. |
| 5,704,371 A | 1/1998 | Shepard |
| 5,710,551 A | 1/1998 | Ridgeway |
| 5,713,485 A | 2/1998 | Liff et al. |
| 5,735,105 A | 4/1998 | Stroud et al. |
| 5,736,580 A | 4/1998 | Huntington et al. |
| 5,737,396 A | 4/1998 | Garcia |
| 5,737,539 A | 4/1998 | Edelson et al. |
| 5,745,366 A | 4/1998 | Higham et al. |
| 5,754,111 A | 5/1998 | Garcia |
| 5,758,095 A | 5/1998 | Albaum et al. |
| 5,764,923 A | 6/1998 | Tallman et al. |
| 5,772,585 A | 6/1998 | Lavin et al. |
| 5,776,783 A | 7/1998 | Kell |
| 5,778,225 A | 7/1998 | Supernaw-Issen et al. |
| 5,781,442 A | 7/1998 | Engleson et al. |
| 5,784,635 A | 7/1998 | McCallum |
| 5,790,409 A | 8/1998 | Fedor et al. |
| 5,797,515 A | 8/1998 | Liff et al. |
| 5,799,981 A | 9/1998 | Tung et al. |
| 5,803,498 A | 9/1998 | Tung et al. |
| 5,805,454 A | 9/1998 | Valerino, Sr. et al. |
| 5,805,676 A | 9/1998 | Martino |
| 5,812,410 A | 9/1998 | Lion et al. |
| 5,822,544 A | 10/1998 | Chaco et al. |
| 5,823,948 A | 10/1998 | Ross, Jr. et al. |
| 5,827,180 A | 10/1998 | Goodman |
| 5,832,449 A | 11/1998 | Cunningham |
| 5,832,450 A | 11/1998 | Myers et al. |
| 5,832,488 A | 11/1998 | Eberhardt |
| 5,833,599 A | 11/1998 | Schrier et al. |
| 5,835,897 A | 11/1998 | Dang |
| 5,836,312 A | 11/1998 | Moore |
| 5,845,255 A * | 12/1998 | Mayaud ..................... 705/3 |
| 5,845,264 A | 12/1998 | Nellhaus |
| 5,950,630 A * | 9/1999 | Portwood et al. .......... 128/897 |
| 6,219,674 B1 * | 4/2001 | Classen ..................... 707/104 |

OTHER PUBLICATIONS

Miller Freeman, Mar. 31, 2001, What to do When a Pharmacist Suspects a Script is Forged, Pulse, London; Issue 486000, pp. 76.*

Miller Freeman, Mar. 31, 2001, "What to do when a pharmacist suspects a script is forged" Pulse, London Issue 00486000, pp. 2.*

* cited by examiner

PRESCRIPTION DATA PROCESSING SYSTEM FOR DETERMINING NEW THERAPY STARTS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

The present invention is related to prescription drugs, and in particular, to a system and method for identifying new therapy starts for a patient based on aggregate information collected for a number of patients over a period of time.

The pharmaceutical industry spends billions of dollars to promote new prescription drugs to physicians, dentists, etc., (collectively referred to as health care specialists) having permission from Drug Enforcement Agency (DEA) to prescribe them. A large portion of the industry's promotional spending budget is allocated to sales representatives and promotional messages. For example, using in-person selling techniques, a pharmaceutical sales representative attempts to persuade a health care specialist to prescribe a new medication (drug) for treating a patient with a particular new ailment or, alternatively, to switch to a new medication which is believed to be more effective than the old one in treating the existing condition.

Typically, the sales representative meets a health care specialist and makes a presentation on the benefits of the new prescription drug, but unlike in standard retail sales, no immediate transaction takes place at the conclusion of the meeting. The success of the sales representative or promotional message is determined only when the health care specialist initially treats the patient with the medication. In this situation, the health care specialist's prescribing behavior may have been affected by the sales representative or by the promotional message, and determining the impact of the sales technique and content is of utmost importance to the pharmaceutical companies. It enables them to optimize marketing strategies and to properly motivate and compensate their sales and marketing forces.

Conventionally, to evaluate the effectiveness of the sales force and promotional messages, newly prescribed drugs are detected on the basis of new prescriptions that may be represented by new pieces of paper. Namely, when presented with a new prescription on a piece of paper, a pharmacist enters information on the prescribed drug into a pharmacist's computer database. This entry is then treated by the pharmaceutical companies as a newly prescribed drug, a so-called new therapy or therapy start. In reality, however, the piece of paper submitted by the patient may have been the prescription for a previous drug, a so-called continuation therapy, presented to the pharmacist to renew or refill the existing medication.

Furthermore, if a patient for various reasons changes pharmacies to fill his/her prescriptions, it appears as if the new therapy has occurred with respect to that patient. That is, when the current pharmacy processes the current prescription, no information is conveyed to the pharmaceutical companies about the patient's previous prescriptions at another pharmacy or pharmacies. Thus, while the prescribed drug is actually a continuation therapy, the pharmaceutical companies are unaware of this situation and regard the prescription as a therapy start.

As explained above, the conventional collection of information on newly prescribed drugs suffers from several disadvantages. A need, therefore, exists for a system and method that overcome the above, as well as other, disadvantages of the conventional techniques.

SUMMARY OF THE INVENTION

It is an object of the present invention to accurately identify new drug therapies for a patient.

It is another object of the present invention to analyze the results and prepare reports on the basis of the drugs identified as new therapy starts.

It is yet another object of the present invention to detect any drug switching within a therapeutic category as undertaken by prescribers.

These and other objects, features and advantages are accomplished by a computer implemented method and system for processing prescription data representing a plurality of prescription drugs. According to the present invention, received prescription data that corresponds to a prescription drug is arranged into a new record of a predetermined format containing an identifier for identifying the patient and further containing a name of the prescription drug. Pre-stored records of the predetermined format are accessed, wherein each pre-stored record contains information on the prescription drugs previously prescribed for respective patients. The identifier in the new record is compared with each identifier located in the pre-stored records to find a matching pre-stored record associated with the patient. The name of the prescription drug is compared with another name of another prescription drug located in the found matching pre-stored record. The prescription drug is identified as newly prescribed for the patient if its name is not substantially identical to the other name.

In accordance with one aspect of the present invention, the predetermined format further contains a date of dispensing the prescription drug to the patient, and contains a dosage of the prescription drug. The last day is calculated when the patient has taken the other prescription based on the date of dispensing and on the dosage if the first and last names are substantially identical. A length of time is then determined that elapsed between the last day of taking the other prescription drug and a first day of dispensing the prescription drug. The prescription drug is identified as newly prescribed for the patient if the determined length of time exceeds a predetermined time interval.

In accordance with another aspect of the present invention, each pre-stored record is obtained for the patient. A list of illnesses is accessed to determine each illness treatable by each respective prescription drug contained in each pre-stored record. Also, the list of illnesses is accessed to determine an illness treatable by the first prescription drug identified as newly prescribed. Subsequently it is ascertained whether the first prescription drug is a replacement for another prescription drug previously taken by the patient.

BRIEF DESCRIPTION OF THE DRAWINGS

The above-mentioned as well as additional objects, features and advantages of the present invention will become readily apparent from the following detailed description thereof which is to be read in conjunction with the accompanying drawings, in which.

In all Figures, like reference numerals represent the same or identical components of the present invention.

DETAILED DESCRIPTION OF THE PREFERRED EMBODIMENTS

As a general overview, the present invention accurately detects any newly prescribed drug by generating records in a database providing unique identifying information for each prescribed drug, whether new or continuing. As the result of the uniquely generated records in the database, the operation of computer-implemented comparison to distinguish between a new therapy and a continuation therapy provides the identification of newly prescribed drugs.

Figure 1:
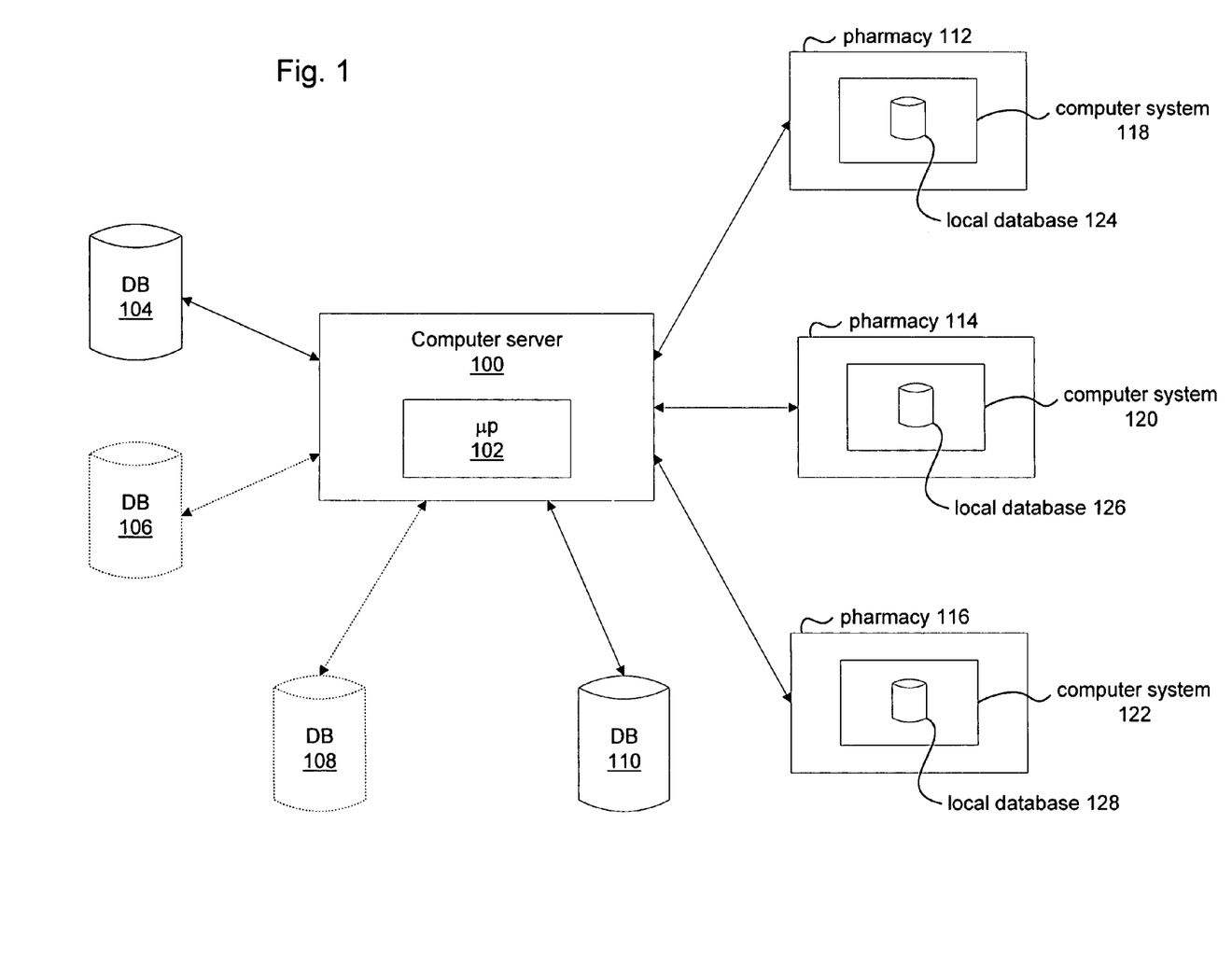
FIG. 1 is a block diagram of a prescription data processing system in accordance with one embodiment of the present invention.

One embodiment of the present invention will now be described in detail with reference to the accompanying figures. In particular, FIG. 1 shows a block diagram of a prescription data processing system in accordance with one embodiment of the present invention. Illustrated in FIG. 1 is a database 104 containing multiple records which will be described in detail below. Connected to the database 104 is a computer server 100 for accessing the records stored in the database 104. The computer server 100 includes a programmable controller, such as a microprocessor 102, for controlling the read, write and other operations associated with the databases as known to those skilled in the art.

Also shown in FIG. 1 are databases 106, 108 illustrated in dashed lines. In another embodiment of the present invention, prescription patient histories may be distributed across several storage devices, such as the databases 104, 106, 108. In accordance with such embodiment, the computer server 100 controls the databases 104, 106 and 108, which all maintain substantially the same structure for data records stored therein, to create an aggregate of the distributed prescription patient histories from all the records contained in the databases.

Further illustrated in FIG. 1 is a database 110 which has a different data structure than the other databases. The database 110 contains a list of substantially every drug in correspondence with illnesses for which the respective drug is prescribed.

FIG. 1 additionally shows pharmacies 112, 114, 116 containing computer systems 118, 120, 122, respectively, for entering data into locally associated databases 124, 126, 128, respectively. Prescription data is supplied, for example, by a pharmacist when presented in-person with a prescription for a drug. After being entered into the computer system 118, 120 or 122 and stored in the local database 124, 126 or 128, respectively, the prescription data is formatted and transferred to the computer server 100 for processing and storage in the remote databases 104, 106, 108 as described below. Alternatively, each computer system 118, 120, 122 in FIG. 1 may be comprised of a so-called "dumb" terminal that does not have any storage capabilities, so that the prescription data is supplied immediately to the computer server 100 without any additional processing (storage) at the pharmacy site. Furthermore, the prescription data may be initially supplied to one or several data warehousing systems interposed between the pharmacies 112, 114, 116 and the computer server 100. After storing a predetermined amount of prescription data, the data warehousing systems send the prescription data at regular time intervals to the computer server 100.

Figure 2:
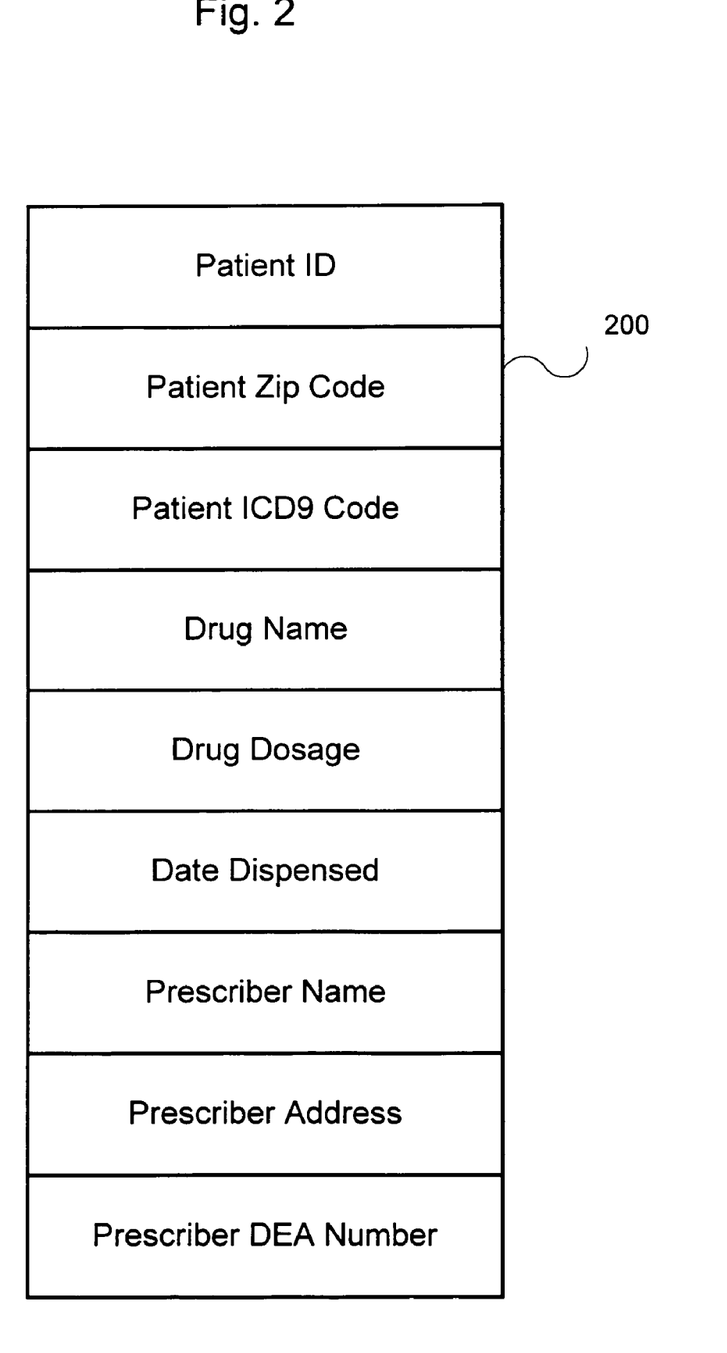
FIG. 2 is a block diagram of a representative record generated by a computer server and stored in a database in the prescription data processing system.

FIG. 2 shows a block diagram of a representative record 200 generated by the computer server 100 and stored in any of the databases 104, 106, 108. The record 200 is generated for each prescribed drug having the following fields: Patient ID, Patient Zip Code, Patient ICD9 Code (medical information history, Drug Name, Drug Dosage, Date Dispensed, Prescriber Name, Prescriber Address, Prescriber DEA Number. It is understood, of course, that additional fields in each database record pertaining to the patient, drug or prescriber may be provided for storing additional if desired.

In accordance with one aspect of the present invention, Patient ID includes a patient identifier, such as a Social Security Number. Any other patient identifier may be used in the Patient ID field, including Patient Name, to uniquely identify the recipient of the prescribed drug. Other fields in the record 200 are self-explanatory and will not be described to avoid detracting from the inventive features of the present invention. It is understood, of course, that the prescriber is any health care specialist, such as physicians, dentists, etc., as mentioned above, with a valid DEA number or medial license.

The operation of the prescription data processing system will now be explained with reference to flowcharts shown in FIGS. 3A and 3B. In step 300, a pharmacist receives a prescription, in paper, electronic or any other media form, for a particular drug from a customer and enters the prescription data, based on the received prescription, using any of the computer systems 118, 120, 122. In step 302, the prescription data received, for example, by the computer system 118 is transmitted to the computer server 100. Any form of data transmission is supported between the computer server 100 and the computer system 118 as known to those skilled in the art.

Figure 3A:
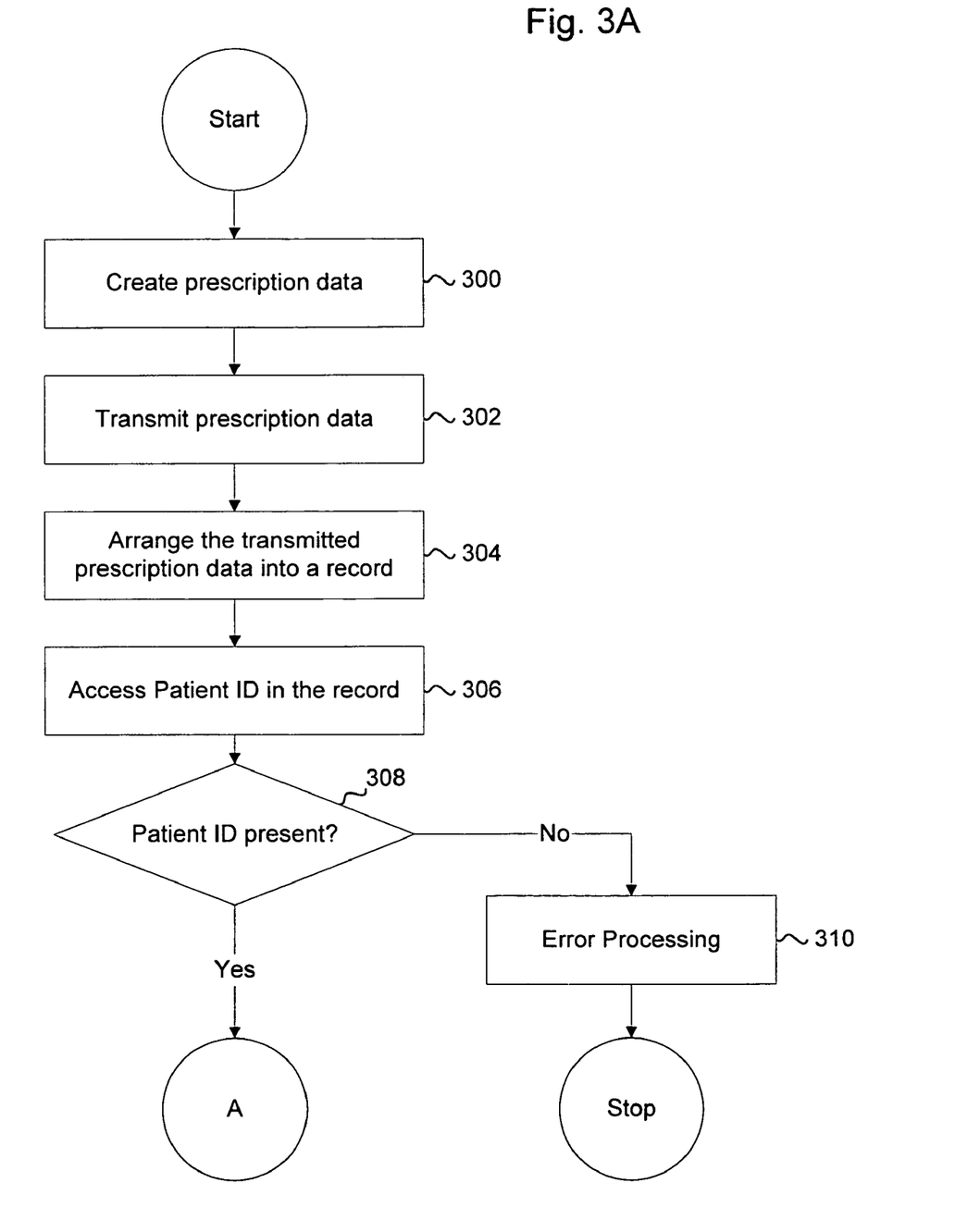
FIGS. 3A and 3B are flowcharts describing the operation of the prescription data processing system.

Further illustrated in FIG. 3A is step 304 in which the computer server 100 receives the transmitted prescription data and arranges the received prescription data into the record 200. Namely, the record 200 having information in the above-described fields is generated on the basis of the received prescription data. Then, the computer server 100 accesses, in step 306, the Patient ID field in the generated record. If the Patient ID field is empty as examined in step 308, the computer server 100 executes an error processing operation in step 310: the record 200 is rejected, or marked as incomplete or fraudulent, and the processing of the record 200 is terminated. It is understood that other error processing operations may be performed in addition to or in place of the above.

Figure 3B:
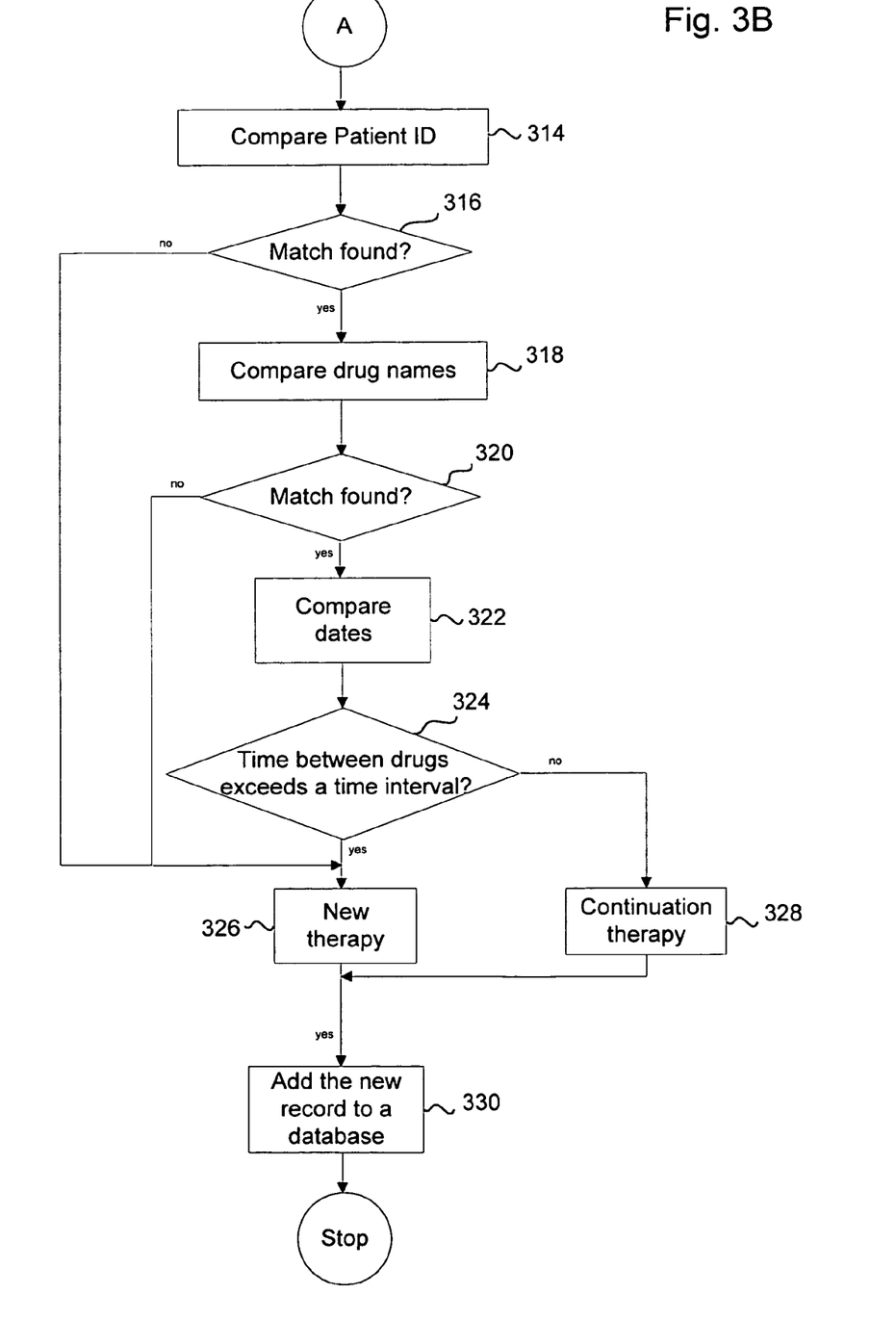

If, however, the Patient ID field in the record 200 contains a valid patient identifier as determined in step 308, the processing operations continue as shown in FIG. 3B. The list of records contains drugs prescribed during a predetermined time interval, such as the last two months for example. In step 314, the patient identifier in the new record is compared to the patient identifiers in the existing database records. Namely, all of the Patient ID fields in the existing database records are examined to determine an identity with the patient identifier in the new record. If there is no match as determined in step 316, the new record representing a newly prescribed drug is identified in the database as a new therapy in step 326. The new record is then added to the database in step 330 as shown in FIG. 3B.

If the match is found in step 316, the processing operation transitions to step 318, where the prescription drug name in the new record is compared with the prescription drug name in the database record with the same patient identifier.

As stated above, in step 318, the prescription drug names for the two records are compared to determine whether the drug names in the Patient ID fields match. In the operation of step 320, the computer server 100 accesses the database 110 to determine the equivalency between the two drug names. For example, some drugs, even though prescribed in their brand names, are often replaced by substitute generic medications to reduce cost. In this situation, even though the drug on the prescription (piece of paper) is brand name, the generic equivalent is typically substituted for the brand name drug by the pharmacist unless the prescriber specifically requests no substitution on the prescription. It is important to note that as the result of such drug substitution, data on the prescribed drug supplied by the pharmacist pertains to the generic medication, as opposed to the brand name. According to one aspect of the present invention, the database 110 is accessed to obtain the equivalency between the brand and generic names of the drug as entered into the computer system 118 by the pharmacist.

Based on the drug equivalency processing using the database 110 as described above, if the equivalency between the drugs is established, then the new prescription record contains the prescribed drug that appears to be a continuation therapy. To confirm this finding, additional operations are performed as follows: the database record is examined for the date that the prescribed drug was dispensed to the patient and the drug dosage in step 322. In particular, information from the Date Dispensed and Drug Dosage fields is extracted. In step 322, the computer server 100 then calculates the last day that the prescribed drug should have been taken by the patient on the basis of the extracted information. Next, the Date Dispensed field is accessed in the new record, and the information likewise is extracted therefrom in step 322. In step 324, the computer server 100 then determines the length of time elapsed between the last day that the prescribed drug was taken by the patient, as determined on the basis of the existing database record, and the first day that the prescribed drug was given to the patient, as determined on the basis of the new record. If the two dates are separated by more than a predetermined time interval, such as 60 days for example, the prescription drug in the new record is considered a new therapy in step 326 and is identified accordingly in the database 104. If, however, this predetermined time interval is not exceeded, then the prescription drug is a continuation therapy as processed in step 328. In any event, the processing of the new record is completed at that point.

Referring back to step 320, if the name of the drug in the new record is not equivalent to the names of drugs in the database records for this patient as determined in step 318, the new prescription is identified as a newly prescribed drug, that is, a new therapy start in step 326. This is indicated in the database record with a logical field (true/false) or any other means as known to those skilled in the art. Following step 326, the computer server adds the new record in step 330 as described above.

In another embodiment of the present invention, the computer server seeks the exact name equivalency between the prescribed drugs. Namely, the database 110 is not accessed to determine whether a particular generic drug has a brand name counterpart. Since only the exact name matches are considered in determining new therapies, this embodiment of the present invention provides a higher level of accuracy in evaluating the effectiveness of the direct sales techniques, promotional messages, etc.

Figure 4:
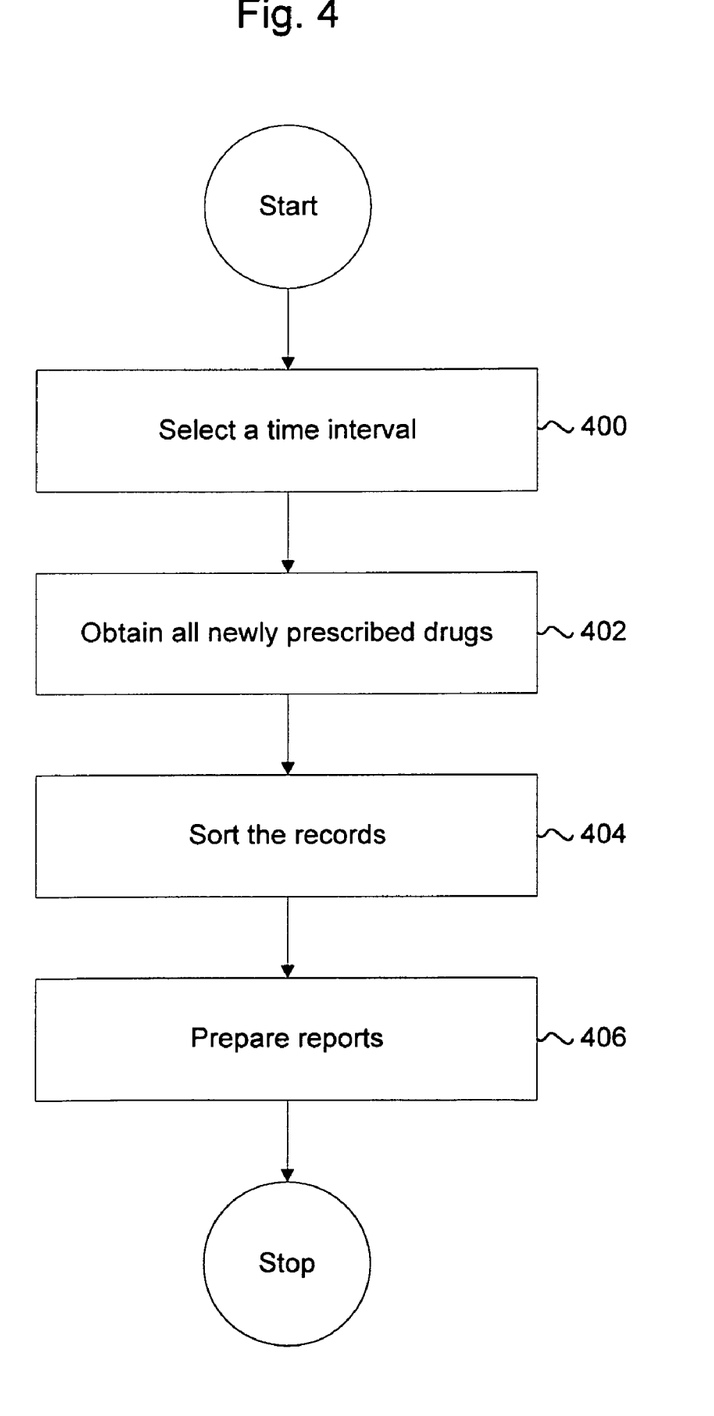
FIG. 4 is a flowchart illustrating various analysis operations and reports prepared by the prescription data processing system in accordance with one embodiment of the present invention.

In another aspect of the present invention, following the processing operations as described above, the newly prescribed drugs as identified by the operations of FIGS. 3A and 3B are analyzed to evaluate the results. FIG. 4 is a flowchart illustrating the analysis operations in accordance with one embodiment.

In step 400, a time interval is selected during which the analysis of results, as obtained in accordance with the present invention and described above, is desired. In step 402, the computer server 100 obtains all records for prescribed drugs identified as new starts during the time interval selected in step 400. Following the processing in step 402, the obtained records are sorted in step 404 according to the information contained in the Prescriber Name, Prescriber Address, and/or Patient Zip Code fields. In step 406, various reports are prepared on the basis of the above sort: the market share of new therapies for a particular drug; the penetration of new therapies in a particular geographic region; the receptiveness of a particular health care provider to new therapies. It is understood that a number of variations on the above, as well as other reports may be prepared by processing the records as described above. Such analysis reports provide tools for adjusting the sales and marketing strategies for new drugs, for accurately compensating the sales representatives, and for taking any other action as deemed by the pharmaceutical company.

Figure 5:
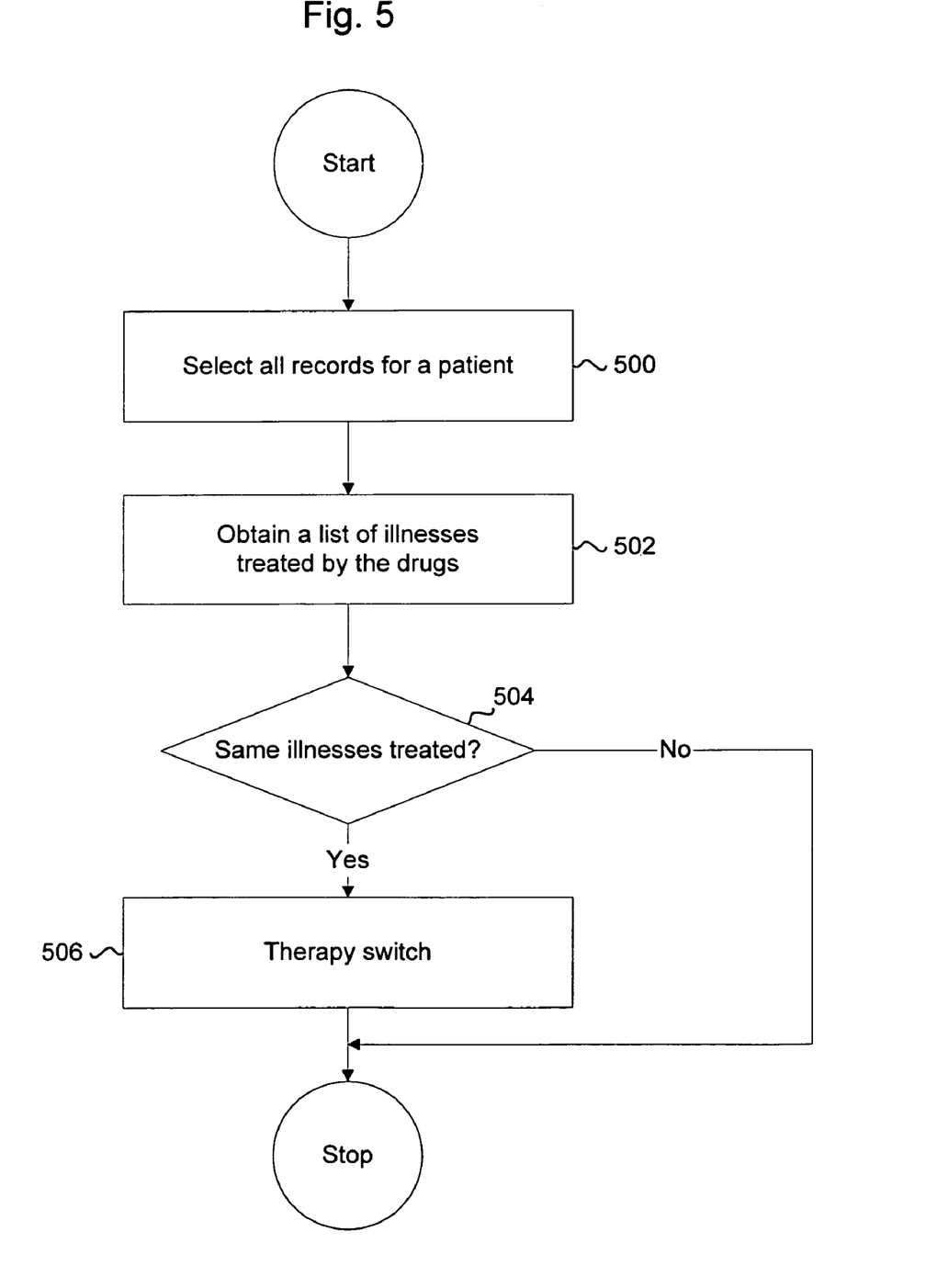
FIG. 5 is a flowchart describing another feature of the prescription data processing system: therapy switching for patients.

Referring to FIG. 5, another feature of the present invention is described next. According to this feature, it is determined whether the newly prescribed drug is a replacement, a so-called therapy switch, for the drug previously given to the patient. In step 500, all records pertaining to a particular patient are accessed on the basis of the Patient ID and selected for further analysis. In step 502, the database 110 is accessed containing substantially all the prescribed drugs in correspondence with illnesses which are treatable by the respective drug. For each of the records selected in step 500 and for the newly prescribed drug, a list of illnesses which are treatable by those drugs is compiled on the basis of the information retrieved from the database 110. In step 504, the comparison is made between the drugs to determine whether the newly prescribed drug treats substantially the same illnesses in the patient as the previously prescribed drugs obtained from the selected database records. If a match is found, the newly prescribed drug is identified as a therapy switch in step 506, and the processing may then continue with steps of FIG. 4. This added information on therapy switching provides an extra tool in identifying and recognizing the successful selling and marketing techniques.

Having described specific preferred embodiments of the invention with reference to the accompanying drawings, it is to be understood that the invention is not limited to those precise embodiments, and that various changes and modifications may be effected therein by one skilled in the art without departing from the scope or the spirit of the invention as defined in the appended claims.

What is claimed is:

1. A computer implemented method for processing prescription data representing a plurality of prescription drugs, said method comprising the steps of:

arranging received prescription data that corresponds to a first prescription drug into a new record of a predetermined format containing an identifier for identifying said patient and further containing a first name of said first prescription drug;

accessing a plurality of pre-stored records of said predetermined format, each pre-stored record containing information on a plurality of prescription drugs previously prescribed for respective patients;

comparing said identifier in said new record with each identifier located in the pre-stored records to find a matching pre-stored record associated with said patient;

comparing said first name of said first prescription drug with a second name of a second prescription drug located in the found matching pre-stored record; and identifying said first prescription drug as a new therapy start for said patient if said first name is not substantially identical to said second name.

2. The method according to claim 1, further comprising determining whether types of said first and second names are brand or generic if said first name is not substantially identical to said second name, converting one of said first and second names to the type of the remaining name if the types are different, and ascertaining an equivalency between said first and second names based on the converted name.

3. The method according to claim 1, further comprising collecting the pre-stored records over a predetermined time interval.

4. The method according to claim 1, wherein said predetermined format further contains a date of dispensing said prescription drug to said patient and a dosage of said prescription drug.

5. The method according to claim 4, further comprising calculating a last day when said patient has taken said second prescription based on said date of dispensing and on said dosage if said first and last names are substantially identical, determining a length of time elapsed between said last day of taking said second prescription drug and a first day of dispensing said first prescription drug, and identifying said first prescription drug as newly prescribed for said patient if said length of time exceeds a predetermined time interval.

6. The method according to claim 4, further comprising obtaining each pre-stored record for said patient, accessing a list of illnesses to determine each illness treatable by each respective prescription drug contained in said each pre-stored record, accessing said list of illnesses to determine an illness treatable by said first prescription drug identified as newly prescribed, and ascertaining whether said first prescription drug is a replacement for another prescription drug previously taken by said patient.

7. The method according to claim 6, further comprising calculating a last day when said patient has taken said another prescription drug based on said date of dispensing and on said dosage, determining a length of time elapsed between said last day of taking said another prescription drug and a first day of dispensing said first prescription drug, and identifying said first prescription drug as said replacement if said length of time does not exceed a predetermined time interval.

8. The method according to claim 1, wherein said predetermined format further contains a prescriber name, a prescriber address, and a patient zip code.

9. The method according to claim 8, further comprising selecting every prescription drug identified as newly prescribed for each patient over a predetermined time interval, and sorting the selected prescription drugs according to at least one criterion selected from the following: a prescriber's name, a prescriber's address, a patient's zip code, a prescriber's specialty, a pharmaceutical sales territory, national-based reporting, ICD9 code.

10. A computer system for processing prescription data representing a plurality of prescription drugs, comprising:

means for arranging received prescription data that corresponds to a first prescription drug into a new record of a predetermined format containing an identifier for identifying said patient and further containing a first name of said first prescription drug;

means for accessing a plurality of pre-stored records of said predetermined format, each pre-stored record containing information on a plurality of prescription drugs previously prescribed for respective patients;

means for comparing said identifier in said new record with each identifier located in the pre-stored records to find a matching pre-stored record associated with said patient;

means for comparing said first name of said first prescription drug with a second name of a second prescription drug located in the found matching pre-stored record; and means for identifying said first prescription drug as a new therapy start for said patient if said first name is not substantially identical to said second name.

11. The system according to claim 10, further comprising means for determining whether types of said first and second names are brand or generic if said first name is not substantially identical to said second name, means for converting one of said first and second names to the type of the remaining name if the types are different, and means for ascertaining an equivalency between said first and second names based on the converted name.

12. The system according to claim 10, further comprising means for collecting the pre-stored records over a predetermined time interval.

13. The system according to claim 10, wherein said predetermined format further contains a date of dispensing said prescription drug to said patient and a dosage of said prescription drug.

14. The system according to claim 13, further comprising means for calculating a last day when said patient has taken said second prescription based on said date of dispensing and on said dosage if said first and last names are substantially identical, means for determining a length of time elapsed between said last day of taking said second prescription drug and a first day of dispensing said first prescription drug, and means for identifying said first prescription drug as newly prescribed for said patient if said length of time exceeds a predetermined time interval.

15. The system according to claim 13, further comprising means for obtaining each pre-stored record for said patient, means for accessing a list of illnesses to determine each illness treatable by each respective prescription drug contained in said each pre-stored record, means for accessing said list of illnesses to determine an illness treatable by said first prescription drug identified as newly prescribed, and means for ascertaining whether said first prescription drug is a replacement for another prescription drug previously taken by said patient.

16. The system according to claim 15, further comprising means for calculating a last day when said patient has taken said another prescription drug based on said date of dispensing and on said dosage, means for determining a length of time elapsed between said last day of taking said another prescription drug and a first day of dispensing said first prescription drug, and means for identifying said first prescription drug as said replacement if said length of time does not exceed a predetermined time interval.

17. The system according to claim 10, wherein said predetermined format further contains a prescriber name, a prescriber address, and a patient zip code.

18. The system according to claim 17, further comprising means for selecting every prescription drug identified as newly prescribed for each patient over a predetermined time interval, and means for sorting the selected prescription drugs according to at least one criterion selected from the following: a prescriber's name, a prescriber's address, a patient's zip code, a prescriber's specialty, a pharmaceutical sales territory, national-based reporting, ICD9 code.

19. A computer-readable storage medium for storing a program code for, when executed, causing a computer to perform a method for processing prescription data representing a plurality of prescription drugs, said method comprising:
   arranging received prescription data that corresponds to a first prescription drug into a new record of a predetermined format containing an identifier for identifying said patient and further containing a first name of said first prescription drug;
   accessing a plurality of pre-stored records of said predetermined format, each pre-stored record containing information on a plurality of prescription drugs previously prescribed for respective patients;
   comparing said identifier in said new record with each identifier located in the pre-stored records to find a matching pre-stored record associated with said patient;
   comparing said first name of said first prescription drug with a second name of a second prescription drug located in the found matching pre-stored record; and
   identifying said first prescription drug as a new therapy start for said patient if said first name is not substantially identical to said second name.

20. A computer implemented method for processing prescription data using a plurality of pre-stored prescription data records, each of which comprises a patient identifier identifying a patient and a drug identifier identifying a drug being prescribed to the identified patient of the respective record, the method comprising:
   receiving a first prescription data record comprising a patient identifier identifying a first patient and a drug identifier identifying a drug being prescribed to the first patient;
   comparing the patient identifier of the first prescription data record to the patient identifier of each of the plurality of pre-stored prescription data records to find a pre-stored prescription data record having a patient identifier matching the patient identifier of the first prescription data record;
   determining whether the drug identifier of the matching pre-stored prescription data record is related to the drug identifier of the first prescription data record;
   identifying the drug being prescribed to the first patient as a new therapy start for the first patient if the drug identifier of the first prescription data record is not related to the drug identifier of the matching pre-stored prescription data record.

21. The method of claim 20, where the step of determining comprises identifying the drug identifier of the matching pre-stored prescription data record as being related to the drug identifier of the first prescription data record if the drug identifier of the matching pre-stored prescription data record matches the drug identifier of the first prescription data record.

22. The method of claim 21, where a drug identifier is of one of two types, one type of drug identifier being an identifier to a brand name drug and the other type of drug identifier being an identifier to a generic drug corresponding to a brand name drug, and where the step of determining comprises:
   prior to the step of identifying, if the drug identifier of the matching pre-stored prescription data record and the drug identifier of the first prescription data record are not of the same type, converting either the drug identifier of the matching pre-stored prescription data record or the drug identifier of the first prescription data record to the other type of drug identifier.

23. The method of claim 22, where a database provides a correspondence between brand name drugs and their corresponding generic drugs, and where the step of converting comprises:
   if the drug identifier being converted is of the type that identifies a brand name drug, searching the database to find the generic drug corresponding to the brand name drug identified by the drug identifier being converted and modifying the drug identifier being converted to identify the found generic drug; and
   if the drug identifier being converted is of the type that identifies a generic drug, searching the database to find the brand name drug corresponding to the generic drug identified by the drug identifier being converted and modifying the drug identifier being converted to identify the found brand name drug.

24. The method of claim 20, where the plurality of pre-stored prescription data records are collected over a predetermined time interval.

25. The method of claim 20, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the method further comprises:
   if the drug identifier of the matching pre-stored prescription data record is related to the drug identifier of the first prescription data record, calculating a last day the drug being prescribed of the matching pre-stored prescription data record was taken based on the dispensing date and drug dosage for the drug being prescribed of the matching pre-stored prescription data record;
   determining a length of time between the last day calculated and the dispensing date of the drug being prescribed of the first prescribed data record; and
   identifying the drug being prescribed to the first patient as a new therapy start for the first patient if the length of time determined exceeds a predetermined time interval.

26. A computer implemented method for processing prescription data using a plurality of pre-stored prescription data records, each of which comprises a patient identifier identifying a patient and a drug identifier identifying a drug being prescribed to the identified patient of the respective record, the method comprising:
   receiving a first prescription data record comprising a patient identifier identifying a first patient and a drug identifier identifying a drug being prescribed to the first patient;

comparing the patient identifier of the first prescription data record to the patient identifier of each of the plurality of pre-stored prescription data records to find all pre-stored prescription data records having a patient identifier matching the patient identifier of the first prescription data record;

identifying all the illnesses treatable by the drug being prescribed of the first prescription data record;

for each matching pre-stored prescription data record, identifying all the illnesses treatable by the drug being prescribed of the respective pre-stored prescription data record; and determining whether the drug being prescribed of the first prescription data record is a therapy switch based on the illnesses treatable by the drug being prescribed of the first prescription and the illnesses treatable by any drug being prescribed of any of the matching pre-stored prescription data records.

27. The method of claim 26, where a database lists the illnesses treatable by drugs, and where the step of identifying all the illnesses treatable by a drug being prescribed comprises:

for a given drug being prescribed, searching the database to find the given drug; and identifying all the illnesses listed in the database as treatable by the found drug.

28. The method of claim 26, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the step of determining comprises:

identifying one of the plurality of pre-stored prescription data records where the drug being prescribed of the identified record treats an illness that the drug being prescribed of the first prescription data record also treats;

calculating a last day the drug being prescribed of the identified record was taken based on the dispensing date and drug dosage for the drug being prescribed of the identified record;

determining a length of time between the last day calculated and the dispensing date of the drug being prescribed of the first prescribed data record; and identifying the drug being prescribed to the first patient as a therapy switch for the first patient if the length of time determined does not exceed a predetermined time interval.

29. The method of claim 26, where the step of deter comprises identifying the drug being prescribed of the first prescription data record as a therapy switch if any illness treatable by the drug being prescribed of the first prescription data record matches any illness treatable by any drug being prescribed of any of the matching pre-stored prescription data records.

30. A computer system for processing prescription data using a plurality of pre-stored prescription data records, each of which comprises a patient identifier identifying a patient and a drug identifier identifying a drug being prescribed to the identified patient of the respective record, the system comprising:

means for receiving a first prescription data record comprising a patient identifier identifying a first patient and a drug identifier identifying a drug being prescribed to the first patient;

means for comparing the patient identifier of the first prescription data record to the patient identifier of each of the plurality of pre-stored prescription data records to find a pre-stored prescription data record having a patient identifier matching the patient identifier of the first prescription data record;

means for determining whether the drug identifier of the matching pre-stored prescription data record is related to the drug identifier of the first prescription data record;

means for identifying the drug being prescribed to the first patient as a new therapy start for the first patient if the drug identifier of the first prescription data record is not related to the drug identifier of the matching pre-stored prescription data record.

31. The system of claim 30, where the means for determining identifies the drug identifier of the matching pre-stored prescription data record as being related to the drug identifier of the first prescription data record if the drug identifier of the matching pre-stored prescription data record matches the drug identifier of the first prescription data record.

32. The system of claim 31, where a drug identifier is of one of two types, one type of drug identifier being an identifier to a brand name drug and the other type of drug identifier being an identifier to a generic drug corresponding to a brand name drug, and where the means for determining comprises:

means for converting either the drug identifier of the matching pre-stored prescription data record or the drug identifier of the first prescription data record to the other type of drug identifier if the drug identifier of the matching pre-stored prescription data record and the drug identifier of the first prescription data record are not of the same type.

33. The system of claim 32, where a database provides a correspondence between brand name drugs and their corresponding generic drugs, and where the means for converting searches the database to find the generic drug corresponding to the brand name drug identified by the drug identifier being converted and modifies the drug identifier being converted to identify the found generic drug if the drug identifier being converted is of the type that identifies a brand name drug, and where the means for converting searches the database to find the brand name drug corresponding to the generic drug identified by the drug identifier being converted and modifies the drug identifier being converted to identify the found brand name drug if the drug identifier being converted is of the type that identifies a generic drug.

34. The system of claim 30, where the plurality of pre-stored prescription data records are collected over a predetermined time interval.

35. The system of claim 30, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the system further comprises:

means for calculating a last day the drug being prescribed of the matching pre-stored prescription data record was taken based on the dispensing date and drug dosage for the drug being prescribed of the matching pre-stored prescription data record if the drug identifier of the matching pre-stored prescription data record is related to the drug identifier of the first prescription data record;

means for determining a length of time between the last day calculated and the dispensing date of the drug being prescribed of the first prescribed data record; and means for identifying the drug being prescribed to the first patient as a new therapy start for the first patient if the length of time determined exceeds a predetermined time interval.

36. A computer system for processing prescription data using a plurality of pre-stored prescription data records, each of which comprises a patient identifier identifying a patient and a drug identifier identifying a drug being prescribed to the identified patient of the respective record, the system comprising:

means for receiving a first prescription data record comprising a patient identifier identifying a first patient and a drug identifier identifying a drug being prescribed to the first patient;

means for comparing the patient identifier of the first prescription data record to the patient identifier of each of the plurality of pre-stored prescription data records to find all pre-stored prescription data records having a patient identifier matching the patient identifier of the first prescription data record;

means for identifying all the illnesses treatable by the drug being prescribed of the first prescription data record;

means for identifying, for each matching pre-stored prescription data record, all the illnesses treatable by the drug being prescribed of the respective pre-stored prescription data record; and means for determining whether the drug being prescribed of the first prescription data record is a therapy switch based on the illnesses treatable by the drug being prescribed of the first prescription and the illnesses treatable by any drug being prescribed of any of the matching pre-stored prescription data records.

37. The system of claim 36, where a database lists the illnesses treatable by drugs, and where the means for identifying all the illnesses treatable by a drug being prescribed comprises:

means for searching the database, for a given drug being prescribed, to find the given drug; and means for identifying all the illnesses listed in the database as treatable by the found drug.

38. The system of claim 36, where the means for determining identifies the drug being prescribed of the first prescription data record as a therapy switch if any illness treatable by the drug being prescribed of the first prescription data record matches any illness treatable by any drug being prescribed of any of the matching pre-stored prescription data records.

39. The system of claim 36, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the means for determining comprises:

means for identifying one of the plurality of pre-stored prescription data records where the drug being prescribed of the identified record treats an illness that the drug being prescribed of the first prescription data record also treats;

means for calculating a last day the drug being prescribed of the identified record was taken based on the dispensing date and drug dosage for the drug being prescribed of the identified record;

means for determining a length of time between the last day calculated and the dispensing date of the drug being prescribed of the first prescribed data record; and means for identifying the drug being prescribed to the first patient as a therapy switch for the first patient if the length of time determined does not exceed a predetermined time interval.

40. A computer program product comprising a computer usable medium having computer readable code embodied therein, the computer readable code, when executed, causing a computer to implement a method for processing prescription data using a plurality of pre-stored prescription data records, each of which comprises a patient identifier identifying a patient and a drug identifier identifying a drug being prescribed to the identified patient of the respective record, the method comprising:

receiving a first prescription data record comprising a patient identifier identifying a first patient and a drug identifier identifying a drug being prescribed to the first patient;

comparing the patient identifier of the first prescription data record to the patient identifier of each of the plurality of pre-stored prescription data records to find a pre-stored prescription data record having a patient identifier matching the patient identifier of the first prescription data record;

determining whether the drug identifier of the matching pre-stored prescription data record is related to the drug identifier of the first prescription data record;

identifying the drug being prescribed to the first patient as a new therapy start for the first patient if the drug identifier of the first prescription data record is not related to the drug identifier of the matching pre-stored prescription data record.

41. The computer program product of claim 40, where the step of determining comprises identifying the drug identifier of the matching pre-stored prescription data record as being related to the drug identifier of the first prescription data record if the drug identifier of the matching pre-stored prescription data record matches the drug identifier of the first prescription data record.

42. The computer program product of claim 40, where a drug identifier is of one of two types, one type of drug identifier being an identifier to a brand name drug and the other type of drug identifier being an identifier to a generic drug corresponding to a brand name drug, and where the step of determining comprises:

prior to the step of identifying, if the drug identifier of the matching pre-stored prescription data record and the drug identifier of the first prescription data record are not of the same type, converting either the drug identifier of the matching pre-stored prescription data record or the drug identifier of the first prescription data record to the other type of drug identifier.

43. The computer program product of claim 40, where a database provides a correspondence between brand name drugs and their corresponding generic drugs, and where the step of converting comprises:
   if the drug identifier being converted is of the type that identifies a brand name drug, searching the database to find the generic drug corresponding to the brand name drug identified by the drug identifier being converted and modifying the drug identifier being converted to identify the found generic drug; and
   if the drug identifier being converted is of the type that identifies a generic drug, searching the database to find the brand name drug corresponding to the generic drug identified by the drug identifier being converted and modifying the drug identifier being converted to identify the found brand name drug.

44. The computer program product of claim 40, where the plurality of pre-stored prescription data records are collected over a predetermined time interval.

45. The computer program product of claim 40, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the method further comprises:
   if the drug identifier of the matching pre-stored prescription data record is related to the drug identifier of the first prescription data record, calculating a last day the drug being prescribed of the matching pre-stored prescription data record was taken based on the dispensing date and drug dosage for the drug being prescribed of the matching pre-stored prescription data record;
   determining a length of time between the last day calculated and the dispensing date of the drug being prescribed of the first prescribed data record; and
   identifying the drug being prescribed to the first patient as a new therapy start for the first patient if the length of time determined exceeds a predetermined time interval.

46. A computer program product comprising a computer usable medium having computer readable code embodied therein, the computer readable code, when executed, causing a computer to implement a method for processing prescription data using a plurality of pre-stored prescription data records, each of which comprises a patient identifier identifying a patient and a drug identifier identifying a drug being prescribed to the identified patient of the respective record, the method comprising:
   receiving a first prescription data record comprising a patient identifier identifying a first patient and a drug identifier identifying a drug being prescribed to the first patient;
   comparing the patient identifier of the first prescription data record to the patient identifier of each of the plurality of pre-stored prescription data records to find all pre-stored prescription data records having a patient identifier matching the patient identifier of the first prescription data record;
   identifying all the illnesses treatable by the drug being prescribed of the first prescription data record;
   for each matching pre-stored prescription data record, identifying all the illnesses treatable by the drug being prescribed of the respective pre-stored prescription data record; and
   determining whether the drug being prescribed of the first prescription data record is a therapy switch based on the illnesses treatable by the drug being prescribed of the first prescription and the illnesses treatable by any drug being prescribed of any of the matching pre-stored prescription data records.

47. The computer program product of claim 46, where a database lists the illnesses treatable by drugs, and where the step of identifying all the illnesses treatable by a drug being prescribed comprises:
   for a given drug being prescribed, searching the database to find the given drug; and
   identifying all the illnesses listed in the database as treatable by the found drug.

48. The computer program product of claim 46, where the step of determining comprises identifying the drug being prescribed of the first prescription data record as a therapy switch if any illness treatable by the drug being prescribed of the first prescription data record matches any illness treatable by any drug being prescribed of any of the matching pre-stored prescription data records.

49. The computer program product of claim 46, where each of the plurality of pre-stored prescription data records further comprises a dispensing date on which the drug being prescribed of the respective record was dispensed and a drug dosage describing the dosage prescribed for the drug being prescribed of the respective record, and where the first prescription data record further comprises a dispensing date on which the drug being prescribed of the first prescription data record was dispensed, and where the step of determining comprises:
   identifying one of the plurality of pre-stored prescription data records where the drug being prescribed of the identified record treats an illness that the drug being prescribed of the first prescription data record also treats;
   calculating a last day the drug being prescribed of the identified record was taken based on the dispensing date and drug dosage for the drug being prescribed of the identified record;
   determining a length of time between the last day calculated and the dispensing date of the drug being prescribed of the first prescribed data record; and
   identifying the drug being prescribed to the first patient as a therapy switch for the first patient if the length of time determined does not exceed a predetermined time interval.

* * * * *